United States Patent [19]

Ricketts

[11] Patent Number: 5,218,344
[45] Date of Patent: Jun. 8, 1993

[54] METHOD AND SYSTEM FOR MONITORING PERSONNEL

[76] Inventor: James G. Ricketts, 5970 N. Echo Canyon Dr., Phoenix, Ariz. 85018

[21] Appl. No.: 738,652

[22] Filed: Jul. 31, 1991

[51] Int. Cl.⁵ ............................................. G08B 21/00
[52] U.S. Cl. .................................... 340/573; 340/539; 340/572; 340/825.31; 379/38
[58] Field of Search ............... 340/573, 539, 574, 572, 340/825.31, 825.32, 825.35, 825.36; 364/409, 413.02, 423

[56] References Cited

U.S. PATENT DOCUMENTS

| | | | |
|---|---|---|---|
| 3,478,344 | 11/1969 | Schwitzgebel et al. | 340/573 |
| 4,347,501 | 8/1982 | Akerberg | 340/539 |
| 4,598,275 | 7/1986 | Ross et al. | 340/573 |
| 4,658,357 | 4/1987 | Carroll et al. | 340/539 |
| 4,706,689 | 11/1987 | Man | 340/539 |
| 4,786,907 | 11/1988 | Koelle | 342/51 |
| 4,814,751 | 3/1989 | Hawkins et al. | 340/573 |
| 4,885,571 | 12/1989 | Pauley et al. | 340/573 |
| 4,897,644 | 1/1990 | Hirano | 340/825.31 |
| 4,918,425 | 4/1990 | Greenberg et al. | 340/573 |
| 4,918,432 | 4/1990 | Pauley et al. | 340/573 |
| 4,952,913 | 8/1990 | Pauley et al. | 340/573 |
| 4,998,095 | 3/1991 | Shields | 340/574 |

FOREIGN PATENT DOCUMENTS

2141006 12/1984 United Kingdom .

Primary Examiner—Glen R. Swann, III
Attorney, Agent, or Firm—Dennis H. Lambert

[57] ABSTRACT

A method and system for monitoring personnel in an institution such as a correctional facility, hospital, school, military installation, and the like, includes a computer connected with one or more stationary transceivers in a defined area of the facility, and a portable transceiver unit worn by each individual who is to be monitored. The computer sends command signals to the stationary transceivers, which broadcast interrogation signals to the portable units. The portable units are configured to respond only to interrogation signals unique to that individual, and upon decoding an interrogation signal incident thereon, broadcast a response signal to the stationary transceivers. The stationary transceivers relay corresponding data to the computer, where the data is analyzed to provide an indication of the number, location and identity of the individuals. The portable transceiver units have an emergency alarm button which may be actuated by the individual in the event of an emergency, and selected portable transceiver units may also be configured to be sensitive to proximity between them. In addition, the portable units may be coded for access to vending apparatus.

17 Claims, 8 Drawing Sheets

METHOD AND SYSTEM FOR MONITORING PERSONNEL

FIELD OF THE INVENTION

This invention relates to a method and system for monitoring personnel. More particularly, the invention relates to a system and method for electronically monitoring the location and identity of individuals from a remote station, and especially for locating, identifying and counting individuals in correctional facilities.

BACKGROUND OF THE INVENTION

Prison populations have increased dramatically in recent years, resulting in overcrowded, dangerous environments that are difficult to monitor and control.

Personnel involved in operating a prison facility, including officers, administrators and other persons providing inmate care and supervision, are typically understaffed and overworked, and generally find it difficult to perform their responsibilities in a timely and competent manner. As a result, inmates may find it easier to escape during periods when they are less closely observed by correctional officers or other personnel who are distracted from their supervisory duties, and escapes sometimes go unnoticed for an undesirable length of time. Further, inmate assaults have increased out of proportion to the prison population, and are difficult to control. Excessive time is required to simply keep count of the prison population, thereby curtailing the ability to provide rehabilitative and other beneficial programs for the inmate population.

Correctional institutions typically contain exercise facilities, lavatories, showers, classrooms, libraries, dining halls, workshops, cellblocks or housing units, and the like, where inmates sleep and/or spend at least a portion of each day. Any given inmate may spend time in more than one of these facilities during a twenty-four hour period. It is thus very difficult and time consuming to continually monitor the location within the correctional facility of any given inmate. And yet, such monitoring is essential if proper control over the inmate population is to be maintained.

Under current procedures, several inmate counts are taken each day. These counts are taken manually, and preferably at least two of the prison staff are assigned for counting each group of inmates. The system of counts in a typical correctional facility includes: formal counts, taken at predetermined intervals at set times and locations during each twenty-four period in accordance with the policies and procedures of the correctional facility; informal counts, in which an authorized staff member may initiate an unscheduled count of inmates under their supervision to make sure that all inmates are present who are assigned to that staff member; and emergency counts, taken at times other than those specified for regularly scheduled formal counts, requiring the same general criteria as for a formal count, and typically taken when there is reason to believe that an escape may have occurred, or following a major disturbance, or the like.

The count system for any correctional facility should provide for at least four formal counts in each twenty-four hour period, and should be timed to facilitate the performance of routine inmate functions and to cause as little interference as possible with leisure and work programs and the like. While a formal count, in particular, is being taken, there should be no movement of inmates, nor should the person taking the count have his attention distracted from the count. Two staff persons should always take any count made in a dormitory or open type housing unit, and care must be taken to insure that an actual person, as opposed to a dummy, is being counted. When taking counts at night, it is necessary to use a flashlight, and care should be taken in its use to avoid waking or unnecessarily distracting an inmate, while at the same time adequate light must be provided to insure that a dummy is not being counted.

In a medium security prison with an inmate population of 500, there may typically be four cellblocks of seventy-five inmates each, and four dormitories of fifty inmates each. The 300 inmates in the cellblocks require a minimum of four officers to take a count, and the 200 inmates in the dormitories require a minimum of eight officers to take a count. In addition, there are required two control room officers, one shift commander, one administrative captain and one administrative clerk.

The basic requirement of keeping count of the inmates in a correctional facility can thus be seen to require the time and services of a large number of staff personnel, and also is disruptive of other facility functions, including those that are rehabilitative, or otherwise beneficial to the inmates and/or staff.

Even when an accurate count is taken of the number of inmates present, the location within the facility of any given inmate must be determined by actual visual observation of that inmate.

Additionally, it is very difficult or even impossible with current staffing levels to personally monitor each inmate closely enough to avoid assaults among inmates, or to assure the safety of staff personnel moving among the inmate population.

Many inmates, and sometimes a correctional officer or other staff member, are killed or injured each year from assaults by other inmates. One inmate being attacked by another has very little chance of receiving help, since his only means of summoning help is by shouting or otherwise attempting to attract attention. An inmate's call for help is not always heard, however, because of the noisy environment. In many cases, it may become known or suspected that one inmate plans an assault on another inmate before the assault actually occurs. In such situations, there is little that the staff can do except warn the individuals to stay away from one another, and attempt to watch them more closely in an effort to keep them separated, or to assign the potential victim to protective custody status.

A staff member needing help generally must call out for assistance, or rely upon a bulky two-way radio, or a "man down" alarm. A call for help by a staff member does not have much more chance of being heard than that of an inmate, and a two-way radio may be difficult or impossible to use, depending upon the circumstances.

Inmate assaults frequently lead to lawsuits against relevant state agencies, adding significantly to the cost of operating correctional facilities. For instance, 721 inmate lawsuits were filed during 1984 against the Department of Corrections in the state of Washington. During 1989–1990, there were 2,200 new lawsuits filed.

In addition to the major concerns of detention and safety, discussed above, inmates of correctional facilities are generally not permitted to carry money. Accordingly, they are not able to access various vending devices, or commissaries and the like. Further, if they desire special information, such as time to parole, etc., they must approach a staff member and make inquiries. This information is not always readily available, and personal time and effort is required from staff members in order to deliver the requested information, service or goods to the inmate.

Examples of prior art devices for monitoring personnel are disclosed in U.S. Pat. Nos. 3,478,344 (Schwitzgebel), 4,814,751 (Hawkins, et. al.), 4,885,571 (Pauley, et. al.) and 4,952,913 (Pauley, et. al.).

Schwitzgebel teaches a system in which the individual being monitored carries a portable apparatus including a wrist-mounted code generator unit and a separate transceiver unit. The transceiver unit transmits a signal that is modulated by the wrist unit, and this modulated signal is detected by a central processing station, which may include directional antennas. The apparatus associated with each individual may transmit a code unique to that individual, and the central processor interrogates each portable apparatus to determine the location and identity of the individual. This system requires that the apparatus carried by the individual have a relatively powerful energy source, i.e., battery. The portable apparatus also includes a manual alarm that may be activated by the individual.

Hawkins, et. al. teach a system in which each individual carries a transmitter that emits a signal having a distinctive frequency. Receiving antenna elements are positioned at selected locations in the facility for detecting the signals emitted by the transmitter units, and a scanning radio receiver is connected with the antenna system. If an individual moves beyond a predetermined range from the antennas, an alarm is given. If an alarm signal is generated, a second, directional receiver tracks the location of the individual. This system also requires that each portable unit have a relatively strong power supply, since it is continuously transmitting a signal.

The Pauley, et. al. patents both disclose systems for monitoring the presence or absence of an individual at a particular location. This system is used, for example, to determine whether a person under house arrest is present at his designated location. The individual being monitored carries a transmitter which periodically emits a signal to a field monitoring device located at the monitoring location. The field monitoring device, in turn, sends a signal to a central control station. The transmitter or tag carried by the individual includes means for detecting when an attempt is made to remove the tag from the person being monitored.

None of the prior art systems known to applicant teach a method of accurately and quickly obtaining a count of the inhabitants of the institution, while simultaneously being able to locate and identify the individuals, and in which each individual wears means by which that individual can give an alarm in an emergency, and which gives that individual access to vending systems and, further, that can warn the individual of the approach of other individuals.

There is thus need for a simple, economical and effective monitoring system that can count, locate and identify the inhabitants of an institution, while at the same time provide individuals with means for giving an alarm in an emergency, and which gives access to vending systems and can warn individuals of impending danger.

SUMMARY OF THE INVENTION

It is therefore an object of this invention to provide a system for counting inmate population in a correctional facility or other institution, wherein counts can be taken at any time and at any location in the facility, including the yard area, at any desired interval without disturbing inmate activities or requiring the presence of staff personnel to take the count.

Another object is to provide a remotely controlled system operable from a central control station for determining the identity and location of an inmate within a correctional or other facility.

A further object of the invention is to provide a means for automatically warning or alerting an inmate that he is entering or approaching a forbidden zone, such as the wrong housing unit or the perimeter fence of the facility, and the like, and/or that another inmate is approaching him beyond a predetermined threshold.

An even further object is to provide a small, unobtrusive device worn by an inmate or other personnel in a correctional or other facility, that includes means for quickly and easily sending an alarm in the event of an emergency or threatening situation.

A more specific object of the invention is to provide a system for counting, locating and identifying persons within a correctional facility or other institution, wherein each individual carries a detection unit that interacts with one or more transceivers connected to a central processing station to automatically count the individuals at predetermined intervals, or as otherwise determined by staff personnel, to identify and locate them within the facility, to alert the individual that he is entering a forbidden zone or that another individual is approaching beyond a predetermined threshold, and to enable the individual to send an alarm in an emergency or threatening situation.

These and other objects and advantages of the invention are achieved by a system in which a small personnel detection unit is worn by each individual to be monitored. One or more, and preferably three stationary transceivers are placed in predetermined areas, i.e., a housing unit, dining hall, classroom, etc., for interaction with the detection units through ultrasonic, microwave, electromagnetic or other signal means. In response to the interaction between the detection unit and node(s) or transceivers, a signal is transmitted to a central processing unit, where suitable programming can count, locate and identify each detection unit.

The detection units, which can be worn by staff members as well as inmates, are each provided with an alarm button which may be activated by the staff member or inmate in an emergency or threatening situation to summon help. The alarm remains active until disarmed by a special tool, and enables the location and identity of a person sending an alarm to be quickly determined. In addition, the system of the invention can locate and identify other persons in the area.

An important feature of the invention is the ability of the detection units to communicate with one another in accordance with predetermined parameters. This is important in a correctional facility, where one inmate may have threatened another, for example. By properly programming the detection units worn by the individuals involved, each can be alerted to the approach of another beyond a predetermined threshold. Thus, an inmate who has been threatened is warned that the person who made the threat is approaching him. Conversely, if an inmate has been instructed to not approach another inmate, his detection unit can be programmed to alert him that he is approaching that inmate beyond permissible boundaries. The units can also be programmed to alert the person wearing the unit that he is approaching a forbidden area.

Further, the personnel detection units can include means for enabling the person wearing it to access various vending devices, such as telephones, information terminals, food and drink vending machines, commissary items, and the like. An example of a suitable means would be a bar code, similar to that commonly found in supermarkets, which would be read by an appropriate scanner that would feed data to the central processing unit, which would check the availability of the requested item to that particular person, and make the appropriate dispensation, if adequate funds are in that person's account.

All of the above functions, except the sending of an alarm by activating an alarm button, are controlled from a computer and can take place in accordance with a predetermined program. Counts of the inmate population can be taken in a matter of seconds and without interrupting other functions. The location and identity of each person in the facility can be immediately determined and recorded, and assaults among inmates or against staff personnel can be severely curtailed, if not eliminated, since the identity of the person making the assault could be determined from the data recorded by the central computer, thus deterring those who might otherwise commit an assault. In other words, not only is the identity and location of the person sending the alarm known, but the identity and location of all other persons in the immediate area can also be immediately determined and stored in memory for future reference.

Moreover, the presence of inmates or staff members in dining hall lines, commissaries, work programs, rehabilitation or self-improvement programs and training sessions can be detected and recorded. In addition, staff surveillance rounds can be monitored and recorded in the memory of the computer-controlled system for future reference and/or legal proceedings.

BRIEF DESCRIPTION OF THE DRAWINGS

The foregoing as well as other objects and advantages of the invention will become apparent from the following detailed description of the invention, particularly when considered in conjunction with the accompanying drawings, in which like reference characters designate like parts throughout the several views, and wherein.

DETAILED DESCRIPTION OF THE PREFERRED EMBODIMENTS

Referring more particularly to the drawings, a personnel head count, identification and locating system according to the invention is represented generally at 10. As described and illustrated herein, the system is shown in use in a correctional facility for monitoring inmates, although it could be used for monitoring individuals or objects in a variety of places, such as schools, factories, nursing homes, hospitals, military installations, and the like.

The system includes a main computer or central processing unit 11, preferably positioned in a centrally located control room. The computer is hard wired or otherwise suitably connected with a plurality of stationary transceivers 12 located throughout the facility, and each inmate wears a portable transceiver or wrist unit 13, preferably in the form of a wrist unit, that interacts via suitable signals transmitted through the air with one or more stationary transceivers in that person's vicinity.

An important feature of the invention is the ability of the transceiver units 13 to communicate with one another when properly configured. This might be done, for instance, when it is desired to prevent two or more individuals from approaching one another beyond a certain threshold, or to prevent an individual from approaching a forbidden area.

Figure 1:
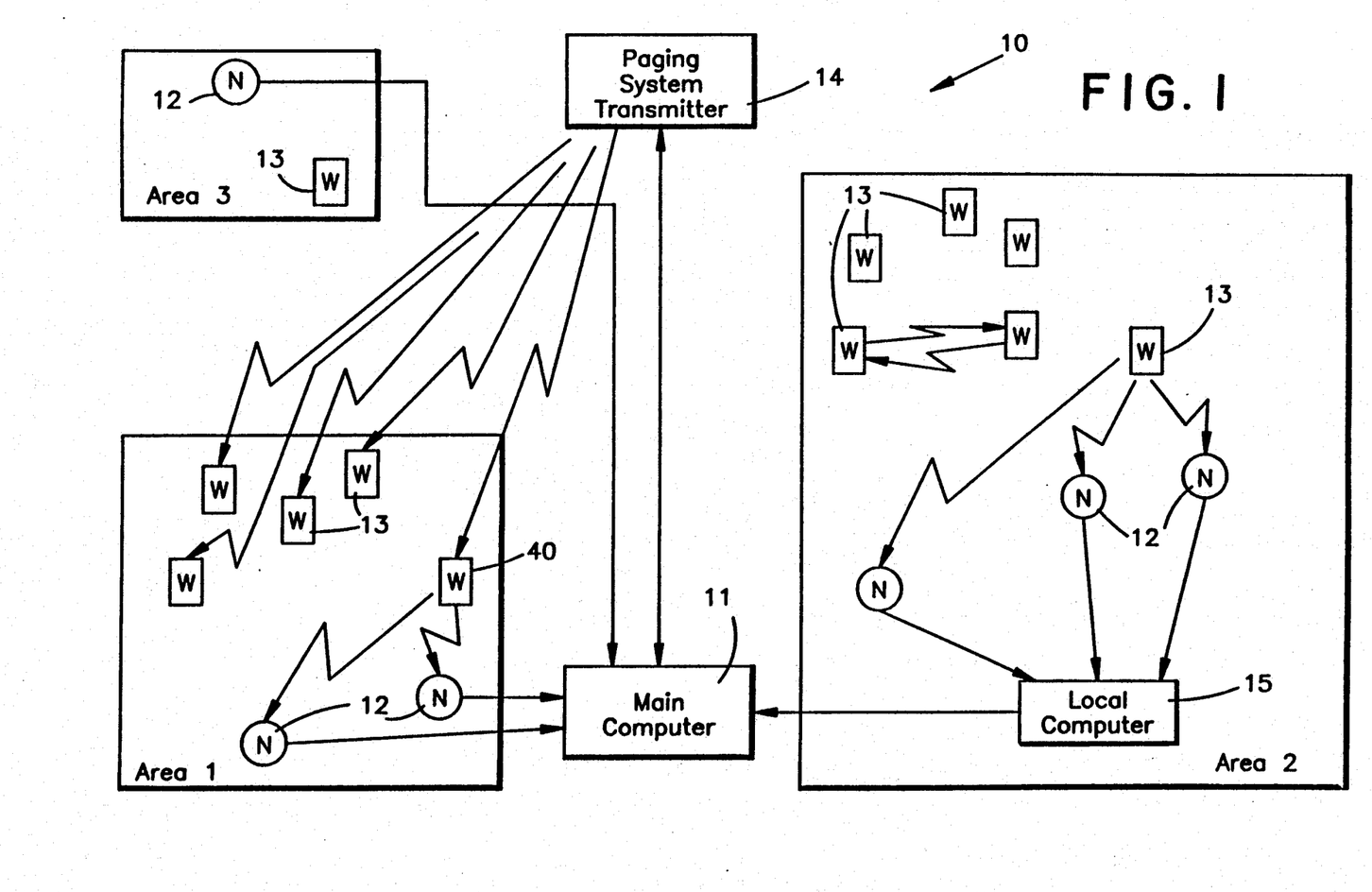
FIG. 1 is a schematic diagram of a typical arrangement of a system in accordance with the invention.

As seen in FIG. 1, a paging system transmitter 14 may be connected with the computer 11 to receive instructions therefrom and to then transmit appropriate signals to the Wrist units 13. As further seen in this figure, a second, local computer 15 may be provided in large areas, such as area 2, to relay signals between the stationary transceivers 12 and the main computer 11.

Figure 3:
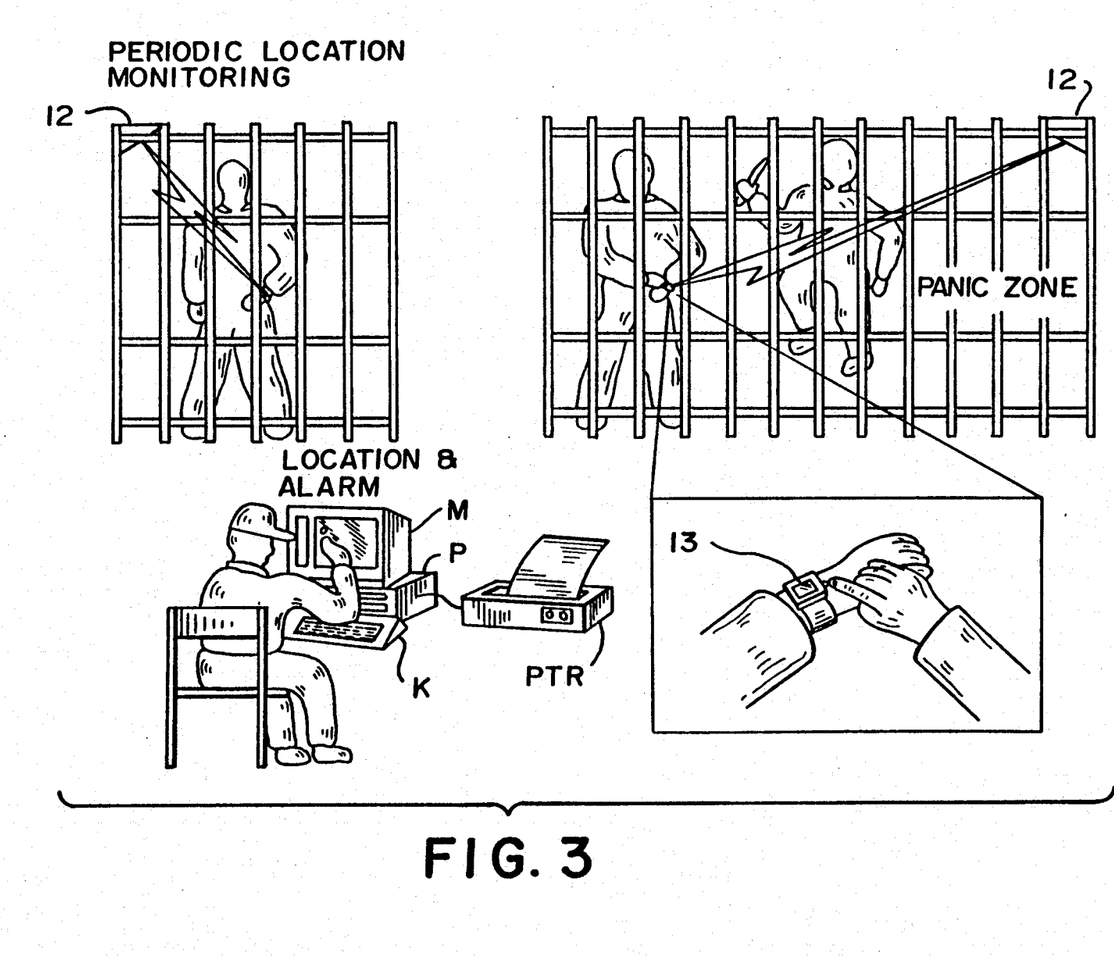
FIG. 3 is a schematic illustration of ways in which the system of the invention may be used to monitor location and to detect and locate the source of an alarm signal.

The computer or computers 11 may comprise conventional PC's, operated by available software, or by software developed for the purpose. Each central or main computer station would, for example, comprise a processor P, monitor M, keyboard K, and a printer PTR (see FIG. 3).

Figure 7:
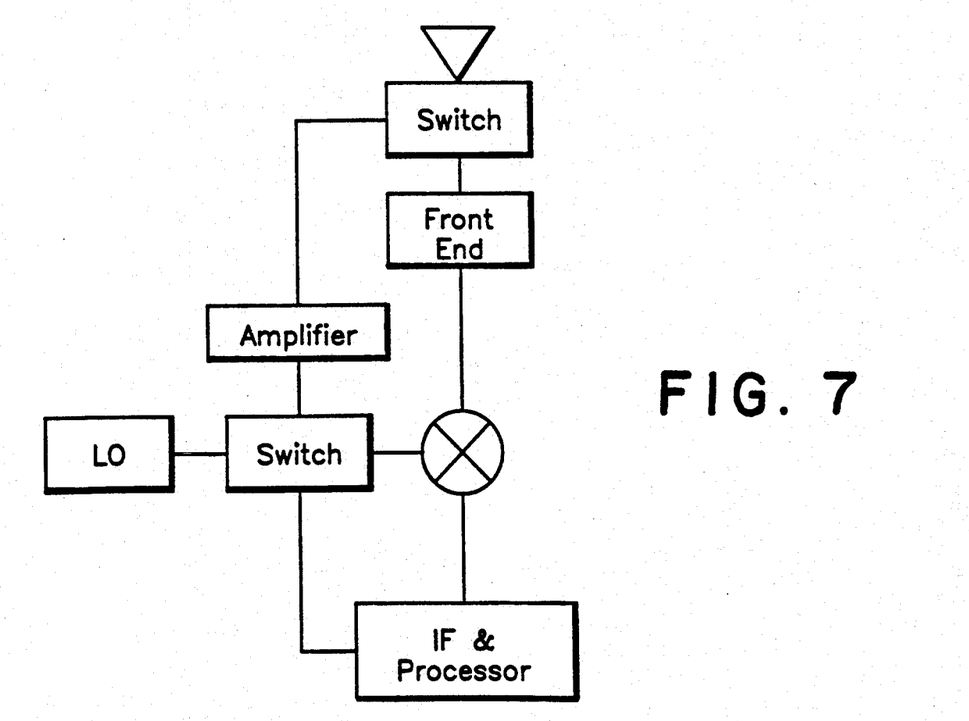
FIG. 7 is a diagrammatic illustration of how a conventional paging device might be modified for adaptation as a wrist unit transceiver according to the invention.
Figure 10:
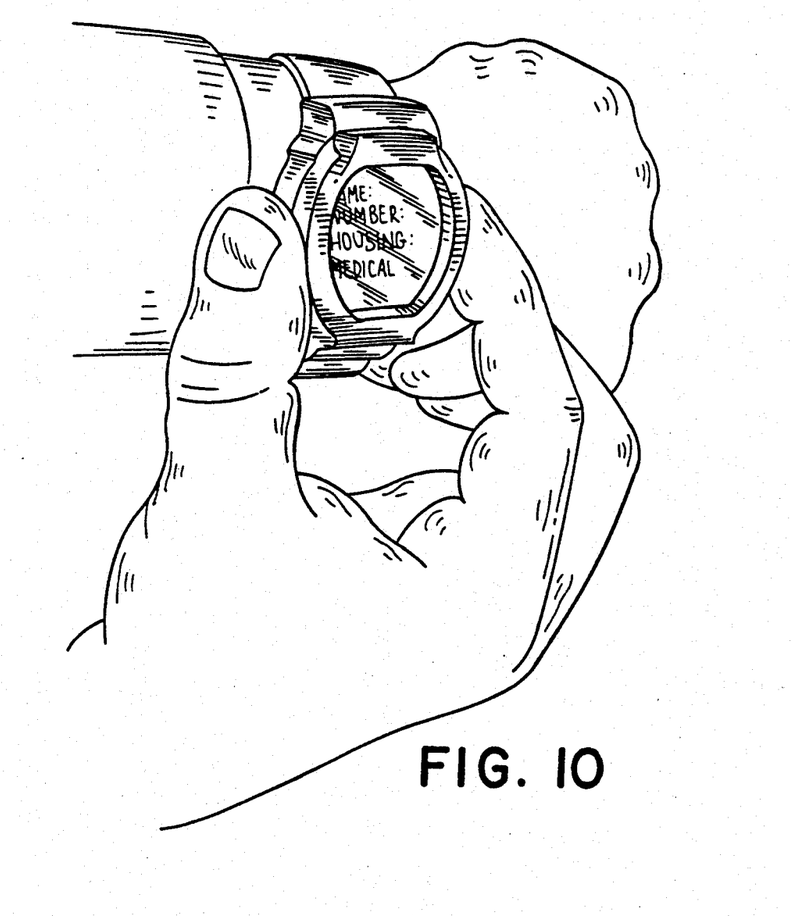
FIG. 10 is a greatly enlarged, schematic perspective view showing how two alarm buttons are required to be activated simultaneously in order to send an alarm.

In one embodiment of the invention, each transceiver wrist unit 13 may comprise an electronic paging device similar to the Motorola wrist watch pager, FCC ID No. AZ489FR3761, with means for generating and modulating a low power (less than 1.0 milliwatt) signal at a frequency of approximately 2,400 MHz (see FIGS. 7 and 10.

Additionally, each wrist unit includes a pair of switches 20 and 22 that cause the circuit in the wrist unit to transmit an alarm signal to the transceivers 12 for relay to the main computer 11. The alarm cannot be turned off by the inmate once it has been energized, and must be deactivated by someone on staff. Upon receipt of this signal, the computer analyzes the transmitted data and determines the location and identity of the person transmitting the alarm signal. It also immediately sends a signal to the transceivers 12 in the area from which the alarm signal was received, which in turn interrogate all other wrist units in the area, thus identifying and locating all other persons in that area. Persons in a position to lend assistance can thus be immediately identified and summoned to the scene. Persons likely to be committing an assault can also be identified for later action, as appropriate.

Those wrist units worn by inmates are also provided with means to prevent removal of the unit. This means may comprise any suitable locking device requiring a special tool to operate. Further, the wrist unit may include means to warn if an attempt is made to remove it from the user. This means may comprise, for example, a wire embedded in the wrist band, or a capacitive circuit utilizing the flesh of the wearer, both operative to generate an alarm signal if the band is broken or removed from the wrist of the person. See, for example, U.S. Pat. Nos. 3,478,344 and 4,885,571. Staff personnel could utilize removable units, if desired.

Each wrist unit can be configured to transmit at a time determined by an interrogation signal imposed on it, either immediately upon receiving the interrogation signal or a predetermined time after receiving the signal.

Moreover, the wrist unit can be configured to generate its own signal, or it can modulate a signal incident upon it. Any of the well known modulation techniques can be used, such as those applied to radar transponders and electronic tag systems (see U.S. Pat. No. 4,786,907, for example). Examples of such techniques include, but are not limited to, shifting the frequency by a predetermined amount, by delaying the incident signal a fixed amount of time, by applying a frequency or phase modulation to an incident continuous wave signal, or by multiplying the incident signal frequency by a predetermined integer value.

If the signal is generated within the wrist unit, it can be a continuous wave, different frequency signal for each inmate. Alternatively, the signal could comprise a short pulse at the same frequency for each user, but at different pulse lengths or at different times for the various users.

Interrogation signals sent to the wrist units can be acoustic, electromagnetic or optical, independent of the type signal to be transmitted by the wrist unit. In the preferred form, the signal is electromagnetic. An electromagnetic wave receiver can have many possible configurations, any of which can be used in the present invention.

If an incident signal is modulated by the wrist unit, the modulated signal can include data indicating the identity of the user, the status of the prime power source, whether the user needs help, and/or whether the unit is in contact with the user's body. This same information, as well as other information, can, of course, be included in any type of signal received from a wrist unit.

Transceivers 12 preferably include a plurality of units A, B and C fixed at spaced locations in an area to be monitored, so that the differences in time required for the signal from a wrist unit 13 to reach the units A, B and C can be measured and used to locate the wrist unit within the area.

The wrist units can be made sensitive to one another by incorporating any of a variety of well known technologies in their circuits. Conventional proximity circuits and alarms, for example, can be incorporated in each wrist unit and arranged to be enabled selectively by staff personnel, so that only selected units will communicate with one another to warn of the mutual approach of those units toward each other. Alternatively, the wrist units may include enabling circuitry to make them responsive to suitable, programmed instructions from the central computer, whereby the wrist units communicate through the computer to give proximity warning, rather than communicating directly with one another.

Figure 2:
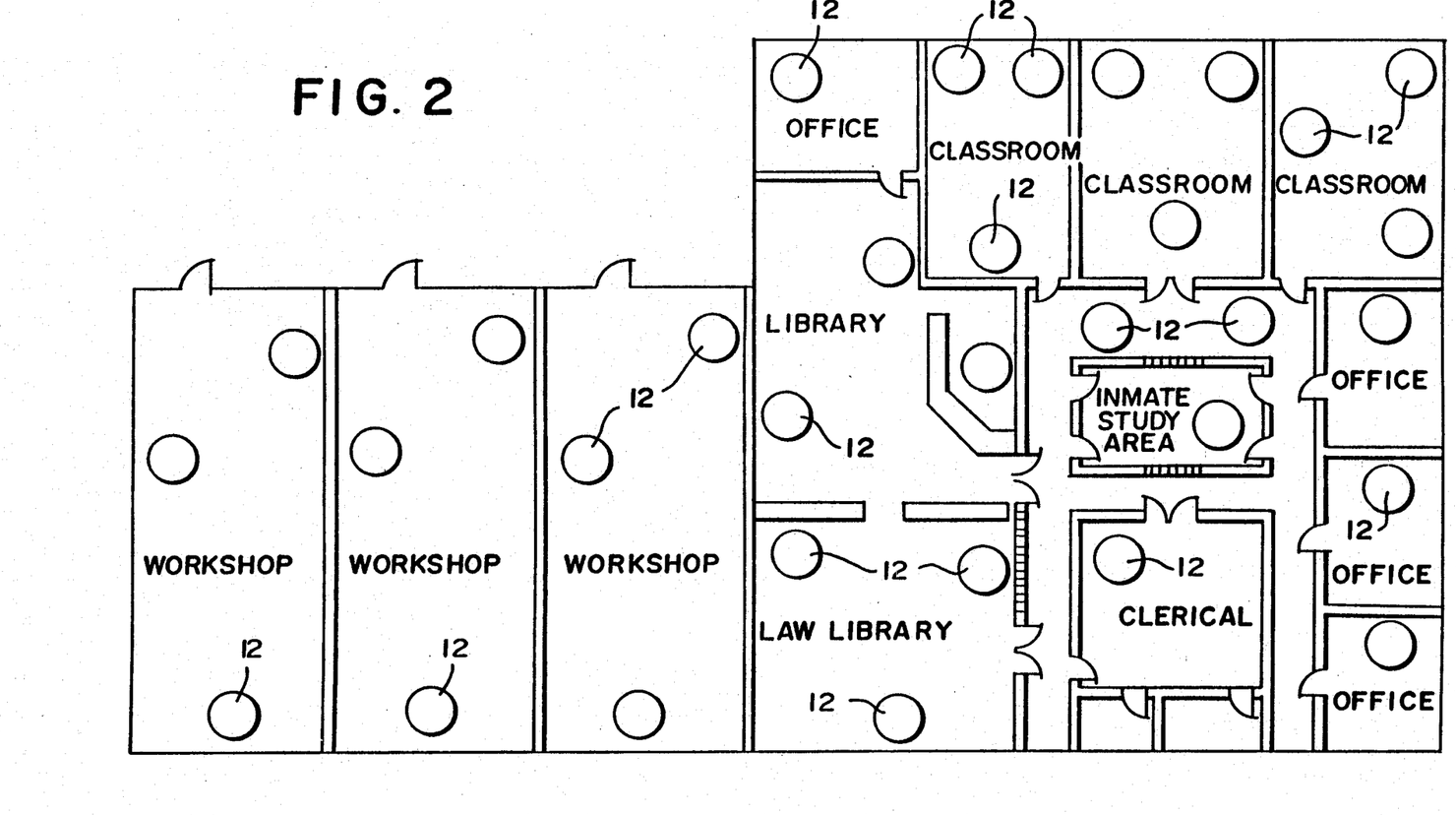
FIG. 2 is a diagrammatic layout of a typical facility environment in which the system of the invention might be used.

The transceivers 12 must be capable of receiving the signal from the Wrist units, and may be of any suitable configuration so long as they match the signal format of the wrist unit. One or more transceivers may be placed in each area of the facility, or one or more transceivers can provide coverage for several areas of the facility. See FIG. 2, for example.

If the wrist units generate their own signal, then the transceivers need only receive this signal and need not be capable of generating a signal. However, if the wrist units modulate or modify a signal incident upon them, then the transceivers can generate the signal that is incident upon the wrist units. In the latter instance, the transceivers can function like a radar system. In this manner, location information can be derived by correctly processing the signals received at the transceiver.

As previously indicated, data from the transceivers 12 is coupled to the main computer 11. Although the preferred method of coupling the transceivers to the computer is by hard wiring the components together, the coupling can be acoustic, electromagnetic or optical.

Preferably at least two transceivers 12 are positioned to cover any major area to be monitored, such as a cafeteria, library, workshop, or the like, but only one is necessary in a cell or other small space. Use of at least three transceivers to cover a major area provides more definitive location data with respect to an individual being monitored.

Location can be determined by a variety of methods. For instance, by analyzing which receivers or transceivers were able to receive data from a specific wrist unit, that unit can be determined to be in the vicinity of those transceivers. The absolute time that it takes a signal to reach multiple transceivers from a specific wrist unit can be analyzed to determine the range of the unit from the transceivers, thereby locating the wrist unit. If this difference in range is known for two transceivers, for example, the position of a specific wrist unit can be located on a three dimensional surface in space. If this difference in range is known for three transceivers, the position of the wrist unit can be determined on a three dimensional line in space. And, if the difference in range is known for four or more transceivers, the absolute position of the wrist unit can be determined.

When the receiver portion of the system functions as radar, it is possible to provide data that contains either the range between the receiver portion and the wrist unit, or the angle to the wrist unit. If both range and angle are provided, then the exact location of the wrist unit relative to that transceiver can be determined. If only range data is provided from a single transceiver or node, then the absolute position of a specific wrist unit is known to be on the surface of a sphere centered about that transceiver or node. If range data is provided from two transceivers, then the absolute position of the wrist unit is known to be on a circle defined by the intersection between two spheres centered on the two transceivers. If range data is provided from three transceivers, then the absolute position of the wrist unit is known, or known to be one of two points. Range data from four transceivers will absolutely define the location of a wrist unit.

Figure 4:
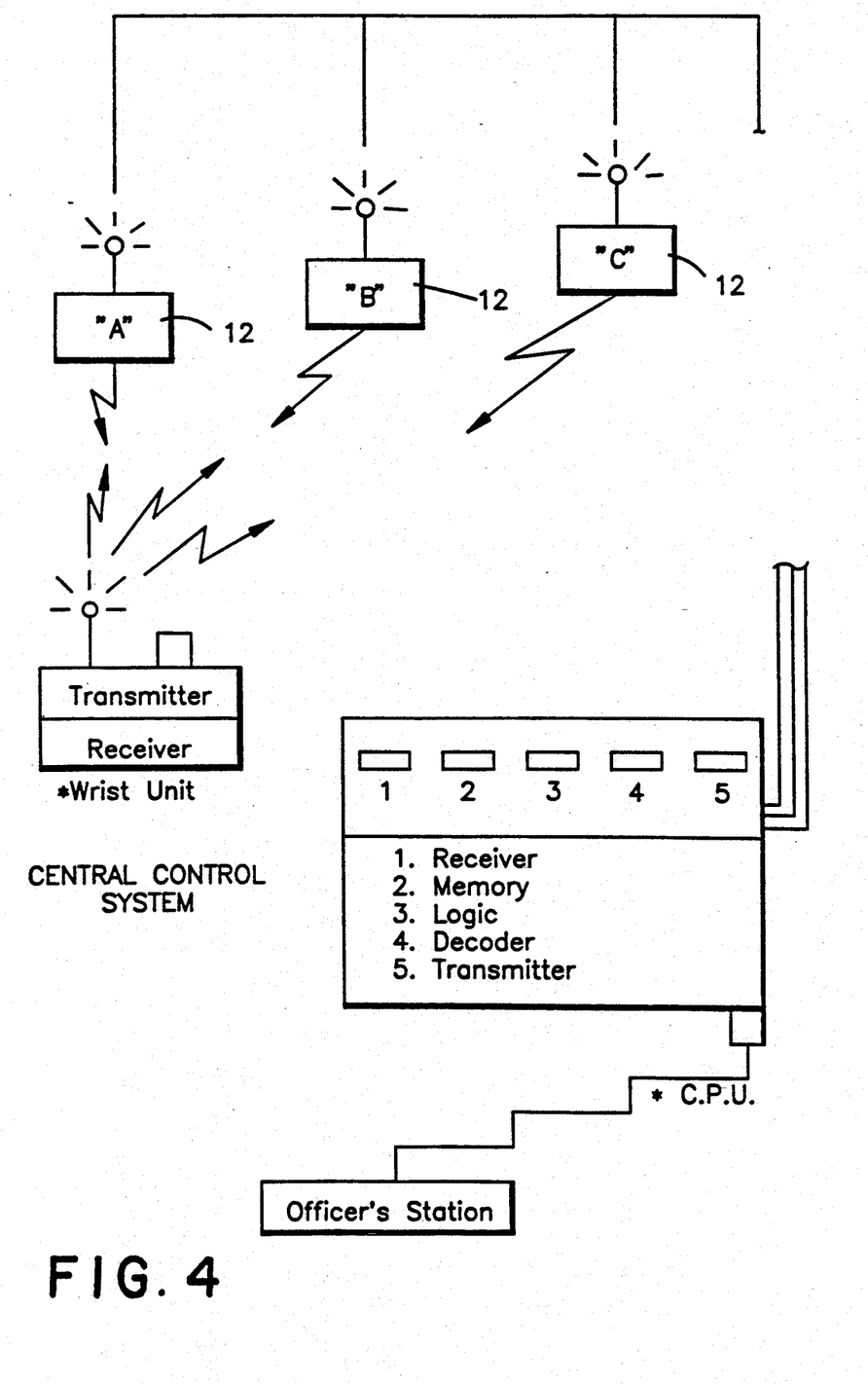
FIG. 4 is a schematic illustration of how the components of the system of the invention might operate in taking a count of individuals in a polled zone.
Figure 5:
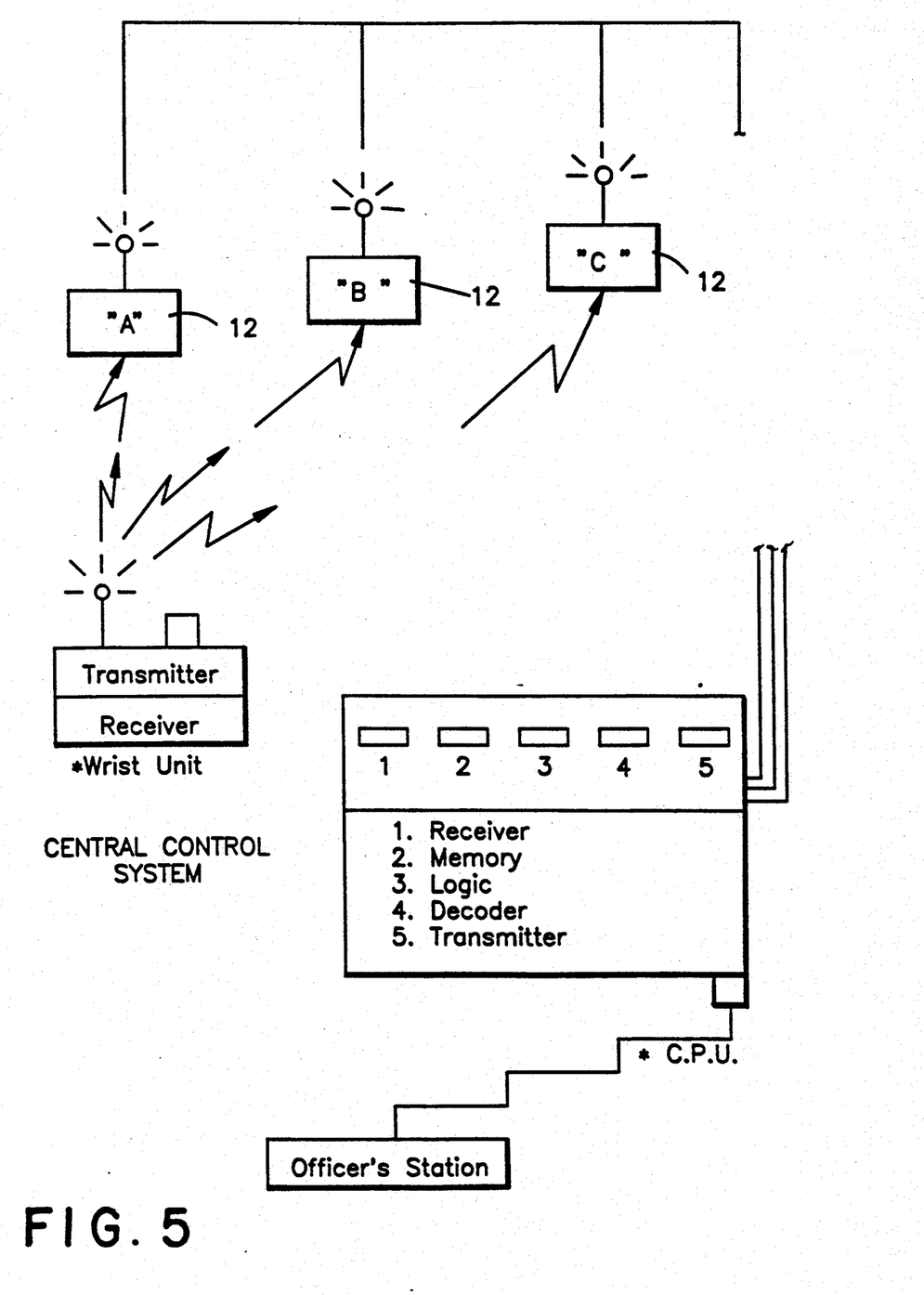
FIG. 5 is a schematic illustration of how the components of the system of the invention might operate when an alarm signal is transmitted.
Figure 6:
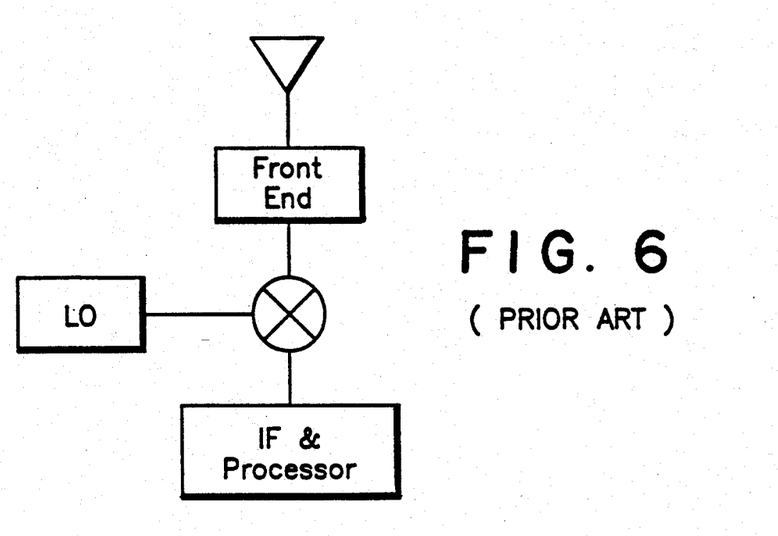
FIG. 6 is a diagrammatic illustration of a conventional, prior art paging device.

In a typical head count operation, the central computer 11 sends a command at a time "T" to the paging transmitter 14 to transmit an interrogation signal to a specific Wrist unit 40. The paging transmitter sends the required signal and also informs the computer that the signal was sent. All wrist units associated with the paging transmitter receive the interrogation signal. However, only unit 40 is able to decode the information.

After unit 40 has decoded the signal, it emits a 2,400 MHz signal, which it amplitude-modulates with the identification number assigned to that unit. The modulated signal also includes a data bit that indicates the status of the power source of that unit.

The signal thus modulated and modified is received by the transceivers 12 that are located in the are a of the wrist unit 40, but this signal is not received by any other transceivers in the facility. The transceivers demodulate the signal from the wrist unit, apply a digital data signal thereto to make the signal compatible with the computer format, and transmit this signal to the computer.

The computer then analyzes this information to determine that the wearer of wrist unit 40 is in area I at time "T". This process is repeated for each wrist unit in the facility until a full count is obtained, taking only a few seconds to complete.

After the computer system has counted and determined the location of each user, it will compare that data with acceptable data stored in memory. If the analyzed data corresponds with the data in memory, the analyzed data is recorded and the computer continues its normal processing of data. If the analyzed data, pertaining to location of a user, for example, does not correspond to the data in memory, the computer will give a visual and/or audible alarm and make a permanent record of the event.

If a signal is not recorded within the prescribed time for all users in the facility, or being counted at that time, the computer generates a visual and/or audible alarm, identifies the specific user for whom a signal was not received, and makes a permanent record of the event. The last known location of that user will also be provided.

Figure 8:
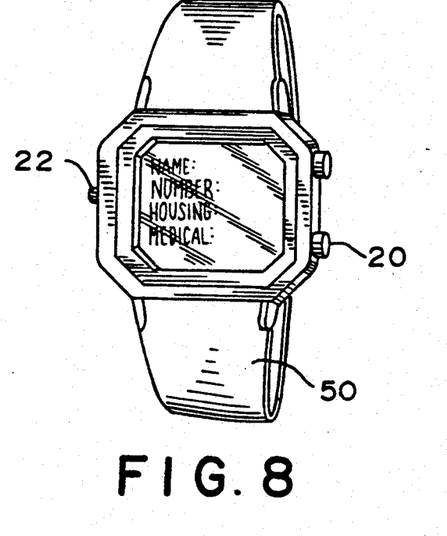
FIG. 8 is a perspective view of a wrist unit in accordance with the invention.
Figure 9:
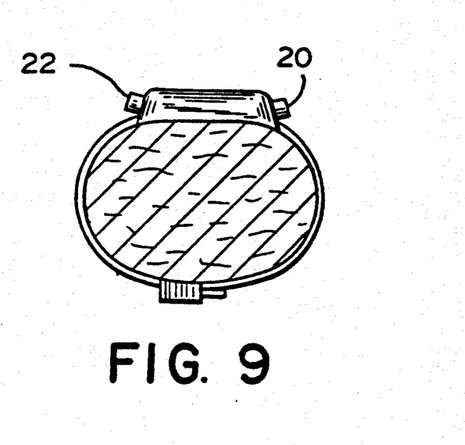
FIG. 9 is a somewhat schematic sectional view showing the unit of FIG. 8 positioned on the wrist of an individual to be monitored.

The wrist units may also be provided with suitable coded means, such as a bar code or the like 50 (see FIG. 8) similar to that found on items in retail stores, for access to vending machines, information terminals, telephones, etc. In use, the individual positions his portable transceiver unit in operative relationship with a scanner of suitable conventional design, which reads the coded information on the wrist unit and relays it to the computer, which analyzes the data to determine whether that individual is permitted access to the requested material, and provides the material when authorized.

Figure 11:
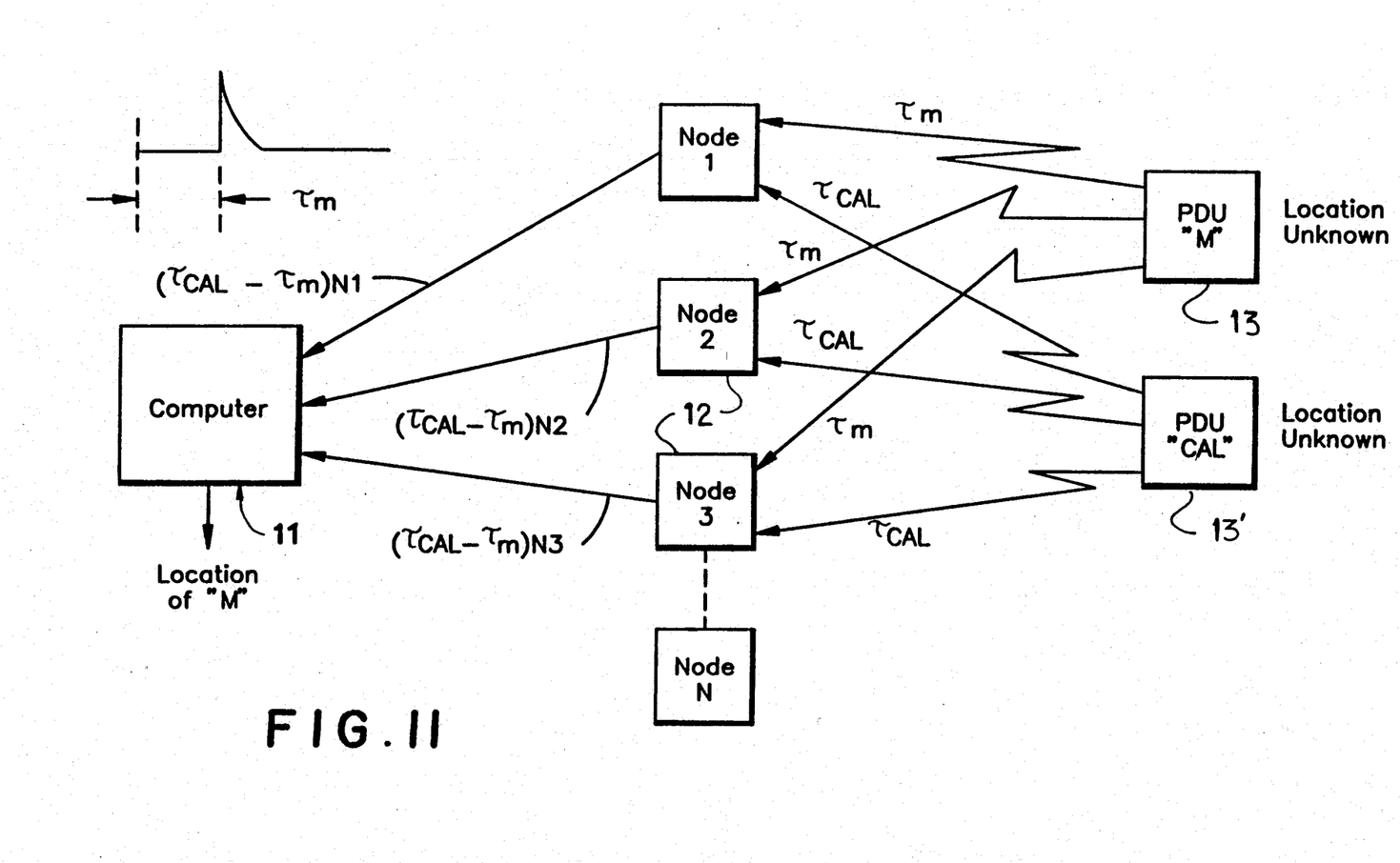
FIG. 11 is a schematic diagram of one example of electronic tracking system for individuals in accordance with the invention.

The block diagram depicted in FIG. 11 shows an arrangement in which a transceiver 13' corresponding to one of the wrist units or portable transceivers is fixed at a known, pre-measured location in an area and the system calibrated using this known location in relation to the fixed nodes or transceivers 12(1 . .. N). Other wrist units 13 in the area are detected by the transceivers 12 and their location determined by differentiating the times required for signals form the transceivers 13 and 13' to reach the transceivers 12.

The system and method of the invention thus provides functions not possible or taught with prior art systems. The invention significantly increases the efficiency and reduces the cost of operation of an institution, especially a correctional facility, by eliminating the need to make a manual count of the inmate population. It also reduces the need for officers to provide inordinately close personal supervision of threatened inmates, and at the same time reduces the incidence and cost of inmate lawsuits stemming from assaults.

Although the invention has been described in detail herein, it is to be understood that numerous variations in design and operation may be made without departing from the spirit and scope of the invention, as defined in the claims appended hereto.

What is claimed is:

1. A method of electronically monitoring the number, location and identity of individuals in an institution such as a correctional facility, hospital, school, and the like, comprising the steps of:

sending commands from a computer to one or more stationary transceivers positioned in an area containing individuals to be monitored;

broadcasting interrogation signals from the stationary transceivers to a plurality of portable transceiver units in the area, each portable unit being secured to an individual to be monitored and each being configured to respond only to an interrogation signal unique to that individual;

decoding the interrogation signals in the portable units, producing a response signal only in those units configured to respond to the interrogation signals, and broadcasting the response signals to the stationary transceivers; and receiving the response signals in the stationary transceivers and relaying corresponding data to the computer, where the data is analyzed to provide an indication of the number, location and identity of the individuals being monitored, wherein the determination of location is based upon the difference in time it takes a signal from a portable transceiver unit to reach the stationary transceivers.

2. A method as claimed in claim 1, including the step of:

providing a selectively operable alarm signal generating means in each portable transceiver unit, that may be activated by the individual wearing that unit to summon help in an emergency.

3. A method as claimed in claim 1, including the steps of:

configuring selected portable transceiver units to be responsive to each other; and producing a signal whenever individuals carrying the selected units approach each other beyond a predetermined threshold.

4. A method as claimed in claim 3, including the step of:

providing a selectively operable alarm signal generating means in each portable transceiver unit, that may be activated by the individual wearing that unit to summon help in an emergency.

5. A method as claimed in claim 1, including the steps of:

providing at least three stationary transceivers in each area to be monitored; and determined the location of individuals in that area by triangulation techniques based on data received by the stationary transceivers from the portable units, and analyzed in the computer.

6. A method as claimed in claim 5, including the step of:

providing a selectively operable alarm signal generating means in each portable transceiver unit, that may be activated by the individual wearing that unit to summon help in an emergency.

7. A method as claimed in claim 6, including the steps of:

configuring selected portable transceiver units to be responsive to each other; and producing a signal whenever individuals carrying the selected units approach each other beyond a predetermined threshold.

8. A method as claimed in claim 3, including the steps of:

providing each selected portable transceiver unit with signal broadcasting and receiving means to render the selected units directly sensitive to the proximity of each other; and producing an alarm signal to the wearer of the selected units whenever they approach one another within a predetermined distance.

9. A method as claimed in claim 3, including the steps of:

using the computer to send interrogation signals to the stationary transceivers for broadcast and receipt of signals between them and selected portable transceiver units, including the broadcast, receipt and analysis of data to indicate the proximity of selected portable units to one another; and providing an alarm signal whenever selected portable units approach each other within a predetermined distance.

10. A method as claimed in claim 9, including the step of:

providing a selectively operable alarm signal generating means in each portable transceiver unit, that may be activated by the individual wearing that unit to summon help in an emergency.

11. A method as claimed in claim 8, including the step of:

providing a selectively operable alarm signal generating means in each portable transceiver unit, that may be activated by the individual wearing that unit to summon help in an emergency.

12. A method as claimed in claim 1, including the step of:

using the portable transceiver unit to access vending means, by providing coded data on each unit and analyzing that data with the computer to determine the availability of the requested vending means to that individual.

13. A system for monitoring individuals in an institution such as a hospital, correctional facility, school and the like, comprising:

a plurality of portable transceiver units each having means for securing it to the person of an individual to be monitored, and each having circuit means operable to respond to an interrogation signal unique to that unit and to broadcast a response to said interrogation signal;

at least one stationary transceiver located in an area where individuals to be monitored may be found, said stationary transceiver having circuit means for broadcasting said interrogation signal and receiving said response; and a computer connected to said stationary transceivers for sending command signals to said stationary transceivers and receiving data therefrom, and operable to analyze said data to provide an indication of the number, location and identity of individuals being monitored, wherein the location is determined by the amount of time it takes a signal from the portable transceiver to reach the stationary transceiver.

14. A system as claimed in claim 13, wherein:

each portable transceiver unit includes circuitry operable to send an alarm signal; and a self-locking alarm button is connected with said circuitry and is actuatable by the individual wearing that unit to energize said circuitry and send an alarm signal to said stationary transceivers to summon help in an emergency.

15. A system as claimed in claim 13, wherein:

means is provided to render selected portable transceiver units sensitive to the proximity of others.

16. A system as claimed in claim 15, wherein:

said means comprises circuit means in each of the selected portable transceiver units to render them directly responsive to the proximity of another of them; and means in said units for giving an alarm when two of said units approach one another within a predetermined distance.

17. A system as claimed in claim 16, wherein:

said means comprises said computer and said stationary transceivers, which collect data indicative of the locations of the selected units, analyze the data to determine the proximity of them to one another, and provide an alarm signal to each of the offending units when they approach each other beyond a predetermined threshold.

* * * * *